United States Patent
Patwardhan et al.

(10) Patent No.: US 9,462,968 B2
(45) Date of Patent: Oct. 11, 2016

(54) SYSTEM AND METHOD FOR ASSESSING BOWEL HEALTH

(71) Applicant: General Electric Company, Schenectady, NY (US)

(72) Inventors: Kedar Anil Patwardhan, Latham, NY (US); David Martin Mills, Niskayuna, NY (US); Jae Hong Kim, Poway, CA (US)

(73) Assignee: General Electric Company, Niskayuna, NY (US)

( * ) Notice: Subject to any disclaimer, the term of this patent is extended or adjusted under 35 U.S.C. 154(b) by 113 days.

(21) Appl. No.: 14/517,024

(22) Filed: Oct. 17, 2014

(65) Prior Publication Data

US 2016/0106347 A1    Apr. 21, 2016

(51) Int. Cl.
| A61B 8/00 | (2006.01) |
| A61B 5/11 | (2006.01) |
| G06T 7/00 | (2006.01) |
| A61B 5/00 | (2006.01) |

(Continued)

(52) U.S. Cl.
CPC ........... *A61B 5/1128* (2013.01); *A61B 5/0263* (2013.01); *A61B 5/1107* (2013.01); *A61B 5/4255* (2013.01); *A61B 5/486* (2013.01); *A61B 6/50* (2013.01); *A61B 8/08* (2013.01); *A61B 8/465* (2013.01); *A61B 8/5223* (2013.01); *A61B 8/565* (2013.01); *G06T 7/0016* (2013.01); *A61B 6/032* (2013.01); *A61B 7/008* (2013.01); *A61B 8/06* (2013.01); *A61B 8/485* (2013.01); *G06T 2207/30092* (2013.01)

(58) Field of Classification Search
CPC A61B 5/0263; A61B 5/1107; A61B 5/1128; A61B 5/4255; A61B 5/486; A61B 6/032; A61B 6/50; A61B 7/008; A61B 8/06; A61B 8/08; A61B 8/465; A61B 8/485; A61B 8/5223; A61B 8/565; G06T 2207/30092; G06T 7/0016
See application file for complete search history.

(56) References Cited

U.S. PATENT DOCUMENTS

| 5,107,842 A | 4/1992 | Levene et al. |
| 5,385,147 A | 1/1995 | Anderson et al. |

(Continued)

FOREIGN PATENT DOCUMENTS

| WO | 0232499 | 4/2002 |
| WO | 2008063249 A2 | 5/2008 |

OTHER PUBLICATIONS

Cooper et al., "Estimating motion in noisy, textured images: optical flow in medical ultrasound", BMVC 1996 Cooper & Graham, 1996, 10 Pages.

(Continued)

*Primary Examiner* — Mark Remaly
(74) *Attorney, Agent, or Firm* — Seema S. Katragadda (57) ABSTRACT

In accordance with one aspect of the present technique, a method includes receiving a plurality of images of an abdominal region from an image capture device. The method further includes identifying a bowel tissue and a peristaltic portion of the bowel tissue from the plurality of images. The method further includes determining a peristalsis property of the bowel tissue based on the peristaltic portion. The peristalsis property includes at least one of a percentage of the peristaltic portion within the bowel tissue and an amount of peristalsis in the peristaltic portion. The method also includes assessing a health the bowel tissue based on the peristalsis property of the peristaltic portion.

12 Claims, 3 Drawing Sheets

(51) Int. Cl.
*A61B 5/026* (2006.01)
*A61B 8/08* (2006.01)
*A61B 6/00* (2006.01)
A61B 6/03 (2006.01)
A61B 7/00 (2006.01)
A61B 8/06 (2006.01)

(56) References Cited

U.S. PATENT DOCUMENTS 5,645,066 A  7/1997  Gandini et al.
8,292,816 B2  10/2012  Yoshimura
8,360,976 B2  1/2013  Imran
2012/0101386 A1  4/2012  Arneson et al.
2012/0184642 A1  7/2012  Bartling et al.

OTHER PUBLICATIONS

Cooper et al., "Estimating Motion in Ultrasound Images of the Small Bowel:Optical Flow without Image Structure", SCIA 2003, LNCS 2749, pp. 571-578.

Cardoso et al., "Nutritional assessment of very low birth weight infants: relationships between anthropometric and biochemical parameters", Nutr Hosp, 2007, vol. 22, Issue 3, pp. 322-329.

SYSTEM AND METHOD FOR ASSESSING BOWEL HEALTH

BACKGROUND

The subject matter disclosed herein generally relates to assessing the health of a bowel tissue. More specifically, the subject matter relates to systems and methods for assessing the health a bowel tissue based on the characteristics and the peristalsis of the bowel tissue.

Doctors, pediatricians, dieticians, and the like often assess the health of a bowel tissue for designing nutritional interventions for preterm and low birth weight infants, patients with, necrotizing enterocolitis, diabetes, eating disorders, and the like. Currently, doctors manually assess the bowel health by counting the number of loops in the bowel tissue that undergo peristalsis from, for example, ultrasound images, x-ray images, and the like. Such methods cause numerous problems as they are qualitative and are dependent on the perception of the doctors.

Thus there is a need for an enhanced system and method for assessing the health of a bowel tissue.

BRIEF DESCRIPTION

In accordance with one aspect of the present technique, a method includes receiving a plurality of images of an abdominal region from an image capture device. The method further includes identifying a bowel tissue and a peristaltic portion of the bowel tissue from the plurality of images. The method further includes determining a peristalsis property of the bowel tissue based on the peristaltic portion. The peristalsis property includes at least one of a percentage of the peristaltic portion within the bowel tissue and an amount of peristalsis in the peristaltic portion. The method also includes assessing a health of the bowel tissue based on the peristalsis property of the peristaltic portion.

In accordance with one aspect of the present system, a system includes a communication module configured to receive a plurality of images of an abdominal region from an image capture device. The system further includes a detection module configured to identify a bowel tissue and a peristaltic portion of the bowel tissue from the plurality of images. The system further includes a scoring module configured to determine a peristalsis property of the bowel tissue based on the peristaltic portion and assess a health of the bowel tissue based on the peristalsis property. The peristalsis property includes at least one of a percentage of the peristaltic portion within the bowel tissue and an amount of peristalsis in the peristaltic portion.

In accordance with another aspect of the present technique, a computer program product encoding instructions is disclosed. The instructions when executed by a processor cause the processor to receive a plurality of images of an abdominal region from an image capture device. The instructions further cause the processor to identify a bowel tissue and a peristaltic portion of the bowel tissue from the plurality of images. The instructions further cause the processor to determine a peristalsis property of the bowel tissue based on the peristaltic portion. The peristalsis property includes at least one of a percentage of the peristaltic portion within the bowel tissue and an amount of peristalsis in the peristaltic portion. The instructions further cause the processor to assess a health of the bowel tissue based on the peristalsis property of the peristaltic portion.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
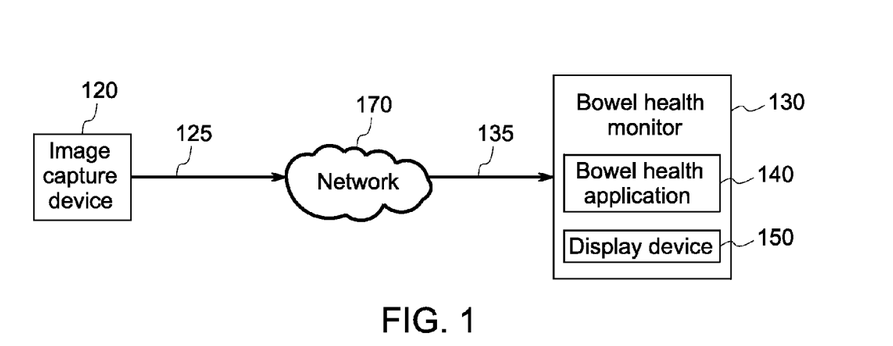
FIG. 1 is a block diagram illustrating a system for assessing a health of a bowel tissue according to one embodiment.

A system and method for assessing a health of a bowel tissue is described herein. The bowel tissue (i.e., the intestine) is the segment of the gastrointestinal tract extending from the stomach to the anus. FIG. 1 illustrates a block diagram of a system 100 configured to assess a health of a bowel tissue according to one embodiment. The illustrated system 100 includes an image capture device 120 and a bowel health monitor 130 that are communicatively coupled via a network 170.

The image capture device 120 may be any type of device that is configured to scan an anatomical part (e.g., abdominal region) of a human and generate a plurality of images of the anatomical part. The image capture device 120 includes, for example, an ultrasound imaging system, a magnetic resonance imaging system, an x-ray imaging system, a computed tomography system, and the like. In one embodiment, the image capture device 120 is an ultrasound imaging system configured to generate two-dimensional (2D) and/or three-dimensional (3D) ultrasound images of an anatomical part. The image capture device 120 is further configured to transmit the plurality of images to the bowel health monitor 130 via the network 170. The image capture device 120 is communicatively coupled to the network 170 via signal line 125. Although one image capture device 120 is coupled to the network 170 in the illustrated embodiment, in other embodiments, a plurality of image capture devices may be coupled to the network 170 to generate the plurality of images and send to the bowel health monitor 130. For example, an anatomical part of a human may be scanned using an ultrasound imaging system and a magnetic resonance imaging system to generate the plurality of images.

The bowel health monitor 130 may be any type of device configured to identify a bowel tissue from a plurality of images received from the image capture device 120 and assess the health of the bowel tissue. In the illustrated system 100, the bowel health monitor 130 includes a bowel health application 140 and a display device 150. The display device 150 is configured to display a user interface including, for example, the bowel tissue and a health score of the bowel tissue. The bowel health application 140 is described below in more detail with reference to FIG. 2. The bowel health monitor 130 is communicatively coupled to the network 170 via signal line 135. Although in the illustrated embodiment, one bowel health monitor 130 is shown, in other embodiments, a plurality of bowel health monitors may be coupled to the network 170. Additionally, although the bowel health monitor 130 is communicatively coupled to the image capture device 120 via the network 170, in other embodiments the processing of the bowel health monitor 130 may be performed within the image capture device 120.

The network 170 may be a wired or wireless type, and may have any number of configurations such as a star configuration, token ring configuration, or other known configurations. Furthermore, the network 170 may include a local area network (LAN), a wide area network (WAN) (e.g., the internet), and/or any other interconnected data path across which multiple devices may communicate. In one embodiment, the network 170 may be a peer-to-peer network. The network 170 may also be coupled to or include portions of a telecommunication network for sending data in a variety of different communication protocols. In another embodiment, the network 170 includes Bluetooth communication networks or a cellular communications network for sending and receiving data such as via a short messaging service (SMS), a multimedia messaging service (MMS), a hypertext transfer protocol (HTTP), a direct data connection, WAP, email, or the like. While only one network 170 is shown coupled to the image capture device 120 and the bowel health monitor 130, multiple networks 170 may be coupled to the entities.

Figure 2:
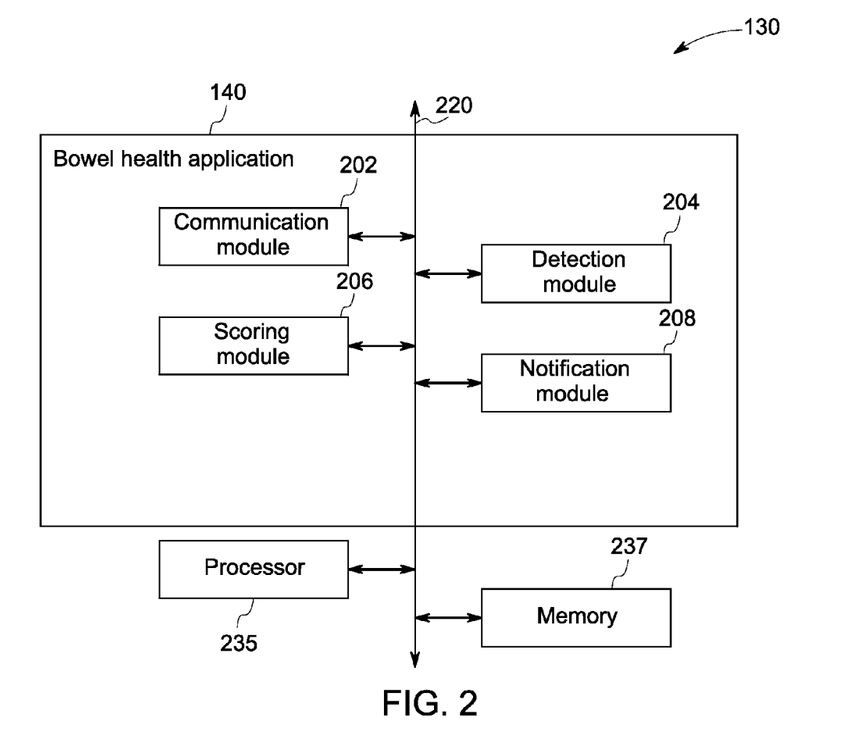
FIG. 2 is a block diagram illustrating a bowel health monitor according to one embodiment.

FIG. 2 is a block diagram illustrating the bowel health monitor 130 according to one embodiment. The bowel health monitor 130 includes the bowel health application 140, at least one processor 235, and a memory 237. The bowel health application 140 includes a communication module 202, a detection module 204, a scoring module 206, and a notification module 208. The modules of the bowel health application 140, the processor 235, and the memory 237 are coupled to a bus 220 for communication with one another.

The processor 235 may include at least one arithmetic logic unit, microprocessor, general purpose controller or other processor arrays to perform computations, and/or retrieve data stored on the memory 237. In another embodiment, the processor 235 is a multiple core processor. The processor 235 processes data signals and may include various computing architectures including a complex instruction set computer (CISC) architecture, a reduced instruction set computer (RISC) architecture, or an architecture implementing a combination of instruction sets. The processing capability of the processor 235 may be limited to supporting the retrieval of data and transmission of data. The processing capability of the processor 235 may also perform more complex tasks, including various types of feature extraction, modulating, encoding, multiplexing, or the like. In other embodiments, other type of processors, operating systems, and physical configurations are also envisioned.

The memory 237 may be a non-transitory storage medium. For example, the memory 237 may be a dynamic random access memory (DRAM) device, a static random access memory (SRAM) device, flash memory or other memory devices. In one embodiment, the memory 237 also includes a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memories (DVD-RAM) device, a digital versatile disc rewritable (DVD-RW) device, a flash memory device, or other non-volatile storage devices.

The memory 237 stores data that is required for the bowel health application 140 to perform associated functions. In one embodiment, the memory 237 stores the modules (for example, the communication module 202, the scoring module 206, and the like) of the bowel health application 140. In another embodiment, the memory 237 stores a bowel threshold value and a motion threshold value that are defined by, for example, an administrator of the bowel health monitor 130. In yet another embodiment, the memory 237 stores historical data that is generated from, for example, previously received clinical data and/or bowel tissue images of relevant patient cohorts. The historical data includes, for example, a prior acoustic response, a prior peristalsis amount, a prior blood flow amount, and a prior blood flow pattern, and the like, that correspond to normal and abnormal bowel tissue. The threshold values and the historical data are described in further detail below with reference to the detection module 204 and the scoring module 206.

The communication module 202 includes codes and routines configured to handle communication between the image capture device and the modules of the bowel health monitor 130. In one embodiment, the communication module 202 includes a set of instructions executable by the processor 235 to provide the functionality for handling communication between the image capture device and the modules of the bowel health monitor 130. In another embodiment, the communication module 202 is stored in the memory 237 and is accessible and executable by the processor 235. In either embodiment, the communication module 202 is adapted for communication and cooperation with the processor 235 and other modules of the bowel health application 140 via the bus 220.

In one embodiment, the communication module 202 receives the plurality of images from the image capture device and sends the plurality of images to the detection module 204. In another embodiment, the communication module 202 receives graphical data for displaying a user interface including a health score of a bowel tissue from the notification module 208. In such an embodiment, the communication module 202 transmits the graphical data to the display device 150 (shown in FIG. 1).

The detection module 204 includes codes and routines configured to identify a bowel tissue and a peristaltic portion of the bowel tissue from the plurality of images. In one embodiment, the detection module 204 includes a set of instructions executable by the processor 235 to provide the functionality for identifying the bowel tissue and a peristaltic portion of the bowel tissue from the plurality of images. In another embodiment, the detection module 204 is stored in the memory 237 and is accessible and executable by the processor 235. In either embodiment, the detection module 204 is adapted for communication and cooperation with the processor 235 and other modules of the bowel health application 140 via the bus 220.

The detection module 204 receives the plurality of images from the image capture device via the communication module 202. For example, the detection module 204 receives a plurality of 2D ultrasound images of a human's abdominal region. The plurality of 2D ultrasound images include a time sequence of images received at a rate of, for example 5-10 2D frames per second within a time duration. Although the detection module 204 and the bowel health application 140 are described below based on 2D ultrasound images according to one exemplary embodiment, in other embodiments, the detection module 204 may receive, for example, 3D ultrasound images or volumes over time, a plurality of images from combination of different imaging modalities, and the like.

The detection module 204 is configured to identify a bowel tissue from at least one of the received plurality of ultrasound images in real-time or as a post processing step. In one embodiment, the detection module 204 identifies the bowel tissue by filtering a received ultrasound image using, for example, a vesselness filter, symmetry filter, and the like, to generate a bowel-likelihood image. In such an embodiment, the detection module 204 identifies the pixels of the bowel-likelihood image having values higher than the bowel threshold value as the pixels representing the bowel tissue.

In another embodiment, the detection module 204 includes a bowel classifier to identify the bowel tissue from the plurality of ultrasound images. In such an embodiment, the detection module 204 receives a plurality of training images in which each pixel is labeled "bowel" or "not bowel" by, for example, a clinical expert or an administrator of the bowel health monitor 130. The detection module 204 extracts a bowel feature vector that includes, for example, gradients, local covariance matrices, local phase estimates, and the like, corresponding to each pixel in the training images. The bowel classifier is then constructed using machine learning algorithms, for example, adaboost algorithm, support-vector machine algorithm, and the like, based on the labels and the bowel feature vector. The bowel classifier then receives an ultrasound image from the communication module 202 and identifies/classifies pixels in the received ultrasound image, which represents the bowel tissue.

The detection module 204 is further configured to determine a peristaltic portion of the bowel tissue from the plurality of images received from the communication module 202. The peristaltic portion is the portion of the bowel tissue that undergoes a peristaltic motion to, for example, propel food through the gastrointestinal tract. In one embodiment, the detection module 204 identifies the peristaltic portion of a bowel tissue by tracking the bowel in a sequence of the received ultrasound images using, for example, a temporal filter, to generate a peristalsis-likelihood image. Each pixel of the peristalsis-likelihood image includes a magnitude of motion of the corresponding pixels in the sequence of ultrasound images. In one embodiment, the detection module 204 calculates the magnitude of motion for a pixel by calculating an average of the motion signal in the corresponding pixels in the sequence of images. The detection module 204 then identifies the pixels of the peristalsis-likelihood image having values higher than the motion threshold value as the pixels representing the peristaltic portion of the bowel tissue. In one embodiment, the detection module 204 is further configured to remove the noise component and the motion component due to breathing of the human from the sequence of images prior to generating the peristalsis-likelihood image.

In another embodiment, the detection module 204 includes a peristalsis classifier to identify the peristaltic portion of the bowel tissue from the plurality of ultrasound images. In such an embodiment, detection module 204 receives a plurality of training images in which each pixel is labeled as "peristalsis" or "not-peristalsis" by, for example, a clinical expert or an administrator of the bowel health monitor 130. the detection module 204 extracts a peristalsis feature vector that includes, for example, temporal gradients, local covariance matrices, local phase gradients over time, dynamic texture features, and the like, corresponding to each pixel in the training images. The peristalsis classifier is then constructed using machine learning algorithms, for example, adaboost algorithm, support-vector machine algorithm, and the like, based on the labels and the peristalsis feature vector. The peristalsis classifier then receives a sequence of ultrasound images from the communication module 202 and identifies/classifies pixels in the sequence of ultrasound of images that represent the peristaltic portion of the bowel tissue.

The detection module 204 is also configured to send bowel data to the scoring module 206. The bowel data includes the plurality of ultrasound images and data indicating the pixels of the plurality of ultrasound images that represent the bowel tissue and the peristaltic portion of the bowel tissue.

The scoring module 206 includes codes and routines configured to assess a health of the bowel tissue. In one embodiment, the scoring module 206 includes a set of instructions executable by the processor 235 to provide the functionality for assessing the health of the bowel tissue. In another embodiment, the scoring module 206 is stored in the memory 237 and is accessible and executable by the processor 235. In either embodiment, the scoring module 206 is adapted for communication and cooperation with the processor 235 and other modules of the bowel health application 140 via the bus 220.

The scoring module 206 receives the bowel data from the detection module 204. The scoring module 206 assesses the health of the bowel tissue by, for example, calculating a health score of the bowel tissue based on the received bowel data. In one embodiment, the scoring module 206 determines a peristalsis property of the bowel tissue from the received bowel data and calculates the health score based on the peristalsis property. The peristalsis property of the bowel tissue includes, for example, a percentage of the peristaltic portion within the bowel tissue, an amount of peristalsis in the peristaltic portion, and the like. For example, the scoring module 206 determines that 20% of the pixels representing the bowel tissue are undergoing peristalsis. In such an example, the scoring module 206 infers that the bowel tissue is abnormal and calculates the health score of the bowel tissue as 20 (out of 100). In another example, the scoring module 206 determines that 75% of the pixels representing the bowel tissue are undergoing peristalsis. In such an example, the scoring module 206 infers that the bowel tissue is normal and calculates the health score of the bowel tissue as 75.

In another example, the scoring module 206 calculates the health score of the bowel tissue by comparing the determined percentage of peristaltic portion with the prior percentage of peristaltic portion stored in the memory 237. If the determined percentage of peristaltic portion in the received ultrasound images matches the prior percentage of peristaltic portion of a normal bowel tissue, the scoring module 206 calculates the health score as, for example, 80. If the determined percentage of peristaltic portion in the received ultrasound images matches the prior percentage of peristaltic portion of an abnormal bowel tissue, the scoring module 206 calculates the health score as, for example, 18.

In another example, the scoring module 206 determines the amount of peristalsis, i.e., an average amount of peristalsis within a region of interest (bowel) as 0.8 mm/second. The scoring module 206 determines the amount of peristalsis based on the magnitude of motion corresponding to each pixel representing the peristaltic portion of the bowel tissue. In such an example, the scoring module 206 infers that the bowel tissue is abnormal and calculates health score of the bowel tissue as 28. In yet another example, the scoring module 206 determines the amount of peristalsis as 2.9 mm/second. In such an example, the scoring module 206 infers that the bowel tissue is normal and calculates the health score of the bowel tissue as 80.

In another example, the scoring module 206 calculates the health score of the bowel tissue by comparing the determined amount of peristalsis with the prior peristalsis amount stored in the memory 237. If the determined amount of peristalsis in the received ultrasound images matches the prior peristalsis amount of a normal bowel tissue, the scoring module 206 calculates the health score as, for example, 78. If the determined amount of peristalsis in the received ultrasound images matches the prior peristalsis amount of an abnormal bowel tissue, the scoring module 206 calculates the health score as, for example, 34.

In another embodiment, the scoring module 206 determines a physical characteristic of the bowel tissue from the received bowel data and calculates the health score based on the physical characteristic. The physical characteristic of the bowel tissue includes, for example, the acoustic response of the bowel tissue, an elasticity of the bowel tissue, and the like. The scoring module 206 calculates the health score of the bowel tissue by comparing the determined physical property with the historical data stored in the memory 237. For example, the scoring module 206 determines the acoustic response of the bowel tissue from the received bowel data. If the determined acoustic response matches a prior acoustic response of an abnormal bowel tissue, the scoring module 206 calculates the health score as, for example, 35. In another example, the scoring module 206 determines the elasticity of the bowel tissue from the received bowel data using common elastography techniques (e.g., shear wave elastography, transient elastography, and the like). If the determined elasticity of the bowel tissue matches a prior elasticity of a normal bowel tissue, the scoring module 206 calculates the health score of the bowel tissue as, for example, 85.

In yet another embodiment, the scoring module 206 determines a blood flow characteristic of the bowel tissue from the received bowel data and calculates the health score based on the blood flow characteristic. The blood flow characteristic of the bowel tissue includes, for example, the amount of blood flow in the bowel tissue, the pattern of blood flow in the bowel tissue, and the like. The scoring module 206 calculates the health score of the bowel tissue by comparing the determined blood flow characteristic with the historical data stored in the memory 237. For example, the scoring module 206 determines the amount of blood flow in bowel tissue from the received bowel data. If the determined amount of blood flow matches a prior blood flow amount of a normal bowel tissue, the scoring module 206 calculates the health score as, for example, 83. In another example, the scoring module 206 determines the pattern of the blood flow by identifying whether the blood flow is towards the bowel tissue, away from the bowel tissue, and the like. If the determined pattern of blood flow matches the prior blood flow pattern in an abnormal bowel tissue, the scoring module 206 calculates the health score of the bowel tissue as, for example, 15.

In yet another embodiment, the scoring module 206 calculates the health score of the bowel tissue based on a weighted ratio of at least one of the peristaltic property, blood flow characteristic, and the physical characteristic of the bowel tissue. For example, the scoring module 206 determines that 80% of the pixels representing the bowel tissue are undergoing peristalsis and the determined elasticity of the bowel tissue matches the prior elasticity of a normal bowel tissue. The scoring module 206 calculates the health score of the bowel tissue as, for example, 90. In any of the above embodiments, the scoring module 206 sends the health score of the bowel tissue and the ultrasound images to the notification module 208.

The notification module 208 includes codes and routines configured to generate and send a notification including the health score of the bowel tissue. In one embodiment, the notification module 208 includes a set of instructions executable by the processor 235 to provide the functionality for generating and sending a notification including the health score of the bowel tissue. In another embodiment, the notification module 208 is stored in the memory 237 and is accessible and executable by the processor 235. In either embodiment, the notification module 208 is adapted for communication and cooperation with the processor 235 and other modules of the bowel health application 140 via the bus 220.

The notification module 208 receives the health score of the bowel tissue and the ultrasound images from the scoring module 206. The notification module 208 generates graphical data for providing a user interface to, for example, an administrator of the bowel health monitor 130. In one embodiment, the user interface includes the health score of the bowel tissue. In another embodiment, the user interface may include an ultrasound image indicating the bowel tissue and/or the peristaltic portion of the bowel tissue, in addition to the health score. In one embodiment, the notification module 208 sends the graphical data to the display device. In such an embodiment, the display device renders the graphical data and displays the user interface. In another embodiment, the notification module 208 sends the notification to an administrator of the bowel health monitor 140 via, for example, e-mail, short messaging service, a voice message, and the like. In either embodiment, the administrator of the bowel health monitor 130 views the user interface and diagnoses the bowel tissue based on, for example, the ultrasound image, the indications of the peristaltic portion, the health score, and the like.

Figure 3:
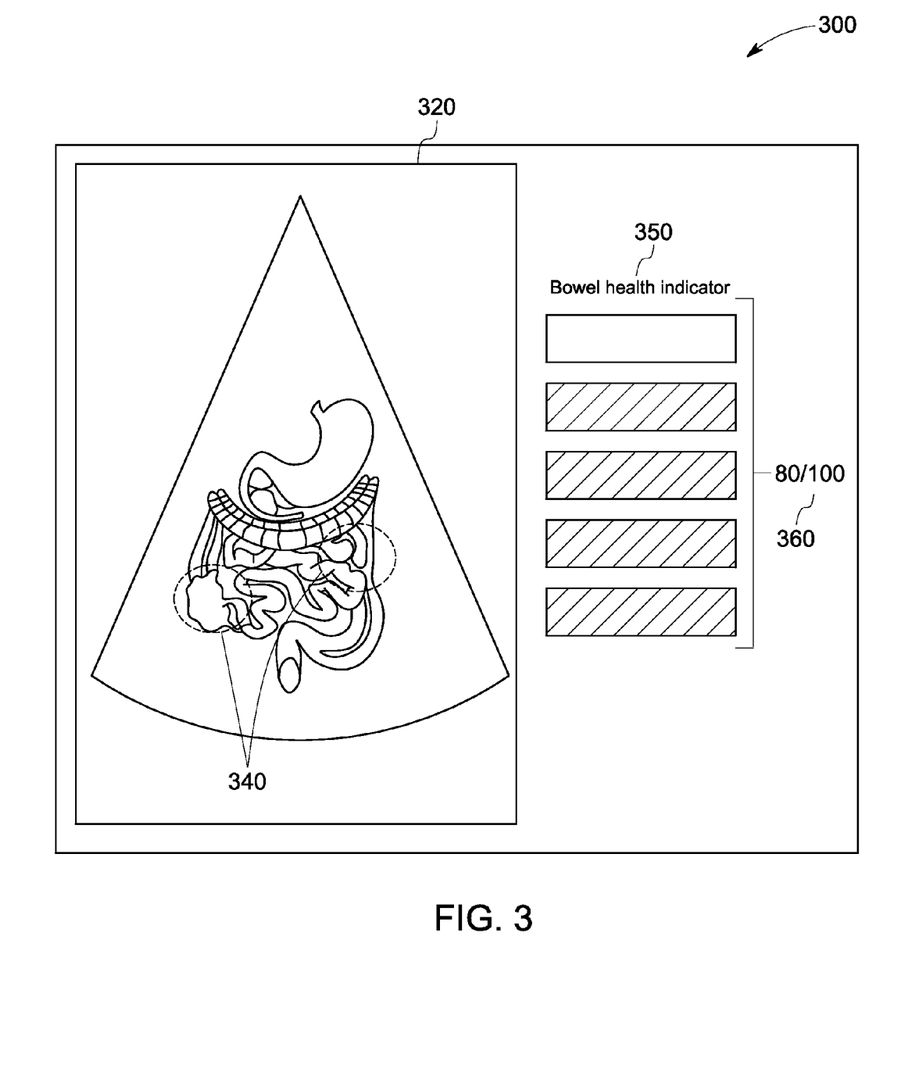
FIG. 3 is a graphical representation of a user interface including a health score of a bowel tissue according to one embodiment.

FIG. 3 is a graphical representation of a user interface 300 including a health score 360 of a bowel tissue according to one embodiment. In the illustrated embodiment, the scoring module calculates that the health score 360 of the bowel tissue as 80. The health score 360 is further depicted by the bowel health indicator 350 in the user interface 300. The user interface 300 further includes an ultrasound image 320 of the bowel tissue. The ultrasound image 320 also indicates the peristaltic portions 340 of the bowel tissue that are identified by the detection module.

Figure 4:
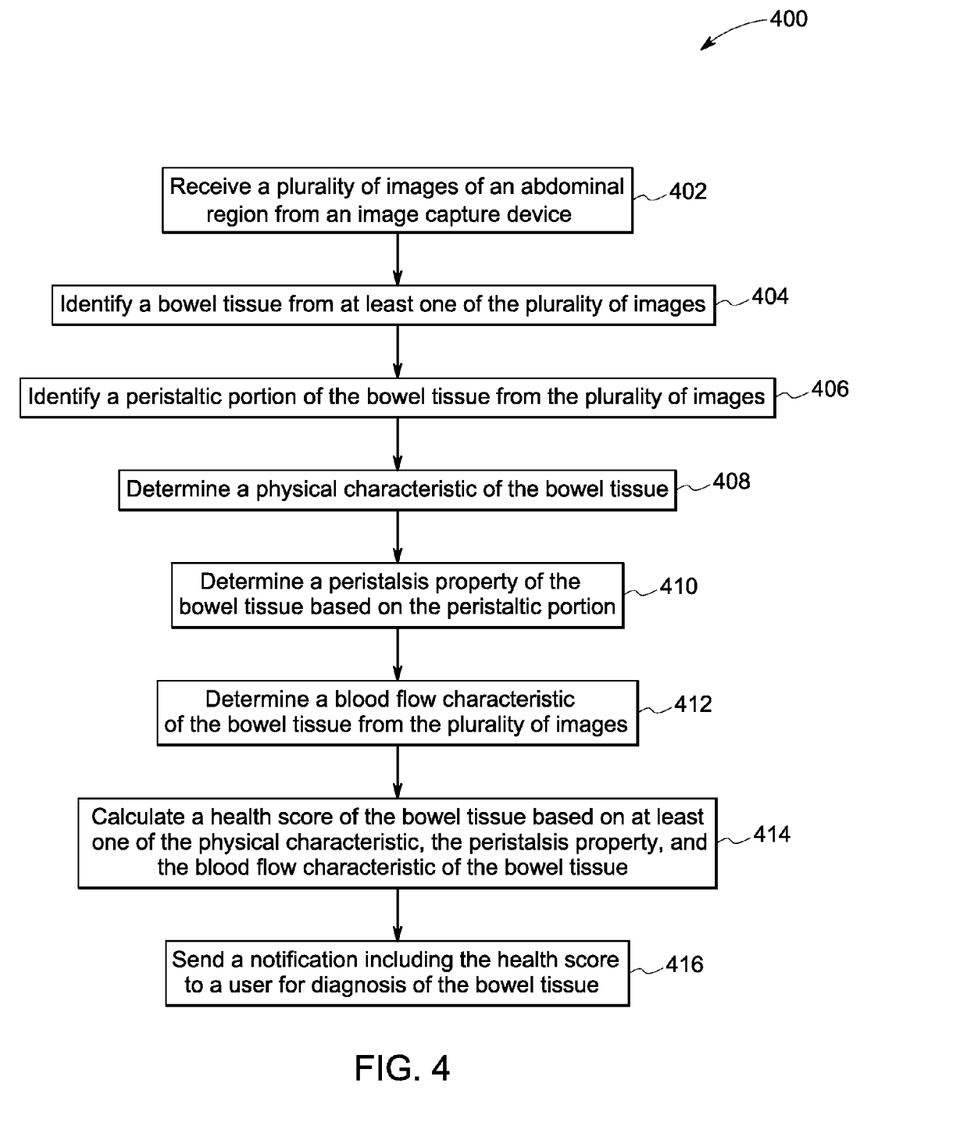
FIG. 4 is a flow diagram illustrating a method for determining a health score of a bowel tissue according to one embodiment.

FIG. 4 is a flow diagram illustrating an exemplary method 400 for calculating a health score of a bowel tissue. The communication module receives a plurality of images of an abdominal region from an image capture device 402. For example, the communication module receives a plurality of ultrasound images of an abdominal region of a patient. The detection module identifies a bowel tissue from at least one of the plurality of images 404. For example, the detection module includes a bowel classifier that identifies pixels in a received ultrasound image that represents the bowel tissue in the abdominal region. The detection module also identifies a peristaltic portion of the bowel tissue from the plurality of images 406. For example, the detection module identifies the peristaltic portion of a bowel tissue by filtering a sequence of the received ultrasound images using a temporal filter. The scoring module determines a physical characteristic of the bowel tissue 408. For example, the scoring module determines an elasticity of the bowel tissue using shear wave elastography. The scoring module also determines a peristalsis property of the bowel tissue based on the peristaltic portion 410. For example, the scoring module determines a percentage of the peristaltic portion within the bowel tissue. The scoring module also determines a blood flow characteristic of the bowel tissue from the plurality of images 412. For example, the scoring module determines the pattern of blood flow in the bowel tissue.

The scoring module calculates a health score of the bowel tissue based on at least one of the physical characteristic, the peristalsis property, and the blood flow characteristic of the bowel tissue 414. In the above described example, the scoring module determines that the elasticity of the bowel tissue, the percentage of the peristaltic portion, and the blood flow pattern match the historical data (i.e., prior elasticity, prior percentage of peristaltic portion, and the prior blood flow pattern) of an abnormal tissue. In such an example, the scoring module calculates the health score of the bowel tissue as 23 (out of 100). The notification module sends a notification including the health score to a user for diagnosis of the bowel tissue 416. For example, the notification module generates graphical data for displaying a user interface to a doctor. The user interface is advantageous as it includes the health score and an image of the bowel tissue, using which the doctor diagnoses the bowel tissue and may design a nutritional intervention for the patient.

Although the bowel health monitor is described above as assessing the health of the bowel tissue by calculating a health score from a plurality of images (e.g., ultrasound images) according to one embodiment, in other embodiments the bowel health monitor may combine health care data (e.g., electrocardiogram, blood oxygen saturation, and the like) with the plurality of images to assess the health of the bowel tissue. In such embodiments, the bowel health monitor may be coupled to sensors (not shown), for example, an electrocardiogram sensor, a pulse oximeter, and the like.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method comprising:
   receiving a plurality of images of an abdominal region from an image capture device;
   identifying a bowel tissue from at least one of the plurality of images;
   identifying a peristaltic portion of the bowel tissue from the plurality of images;
   determining a peristalsis property of the bowel tissue based on the peristaltic portion, wherein the peristalsis property includes at least one of a percentage of the peristaltic portion within the bowel tissue and an amount of peristalsis in the peristaltic portion; and
   assessing a health of the bowel tissue based on the peristalsis property of the peristaltic portion.

2. The method of claim 1, wherein assessing the health of the bowel tissue further comprises calculating a health score of the bowel tissue based on the peristalsis property of the peristaltic portion.

3. The method of claim 2, further comprising:
   determining a physical characteristic of the bowel tissue from the plurality of images; and
   calculating the health score of the bowel tissue based on the physical characteristic.

4. The method of claim 3, wherein the physical characteristic includes at least one of an acoustic response and an elasticity of the bowel tissue.

5. The method of claim 2, further comprising:
   determining a blood flow characteristic of the bowel tissue from the plurality of images; and
   calculating the health score of the bowel tissue based on the blood flow characteristic.

6. The method of claim 5, wherein the blood flow characteristic includes at least one of an amount of blood flow and a pattern of blood flow in the bowel tissue.

7. The method of claim 2, further comprising sending a notification including the health score of the bowel tissue to a user for diagnosis of the bowel tissue.

8. The method of claim 1, wherein the plurality of images include at least one of plurality of ultrasound images, a plurality of magnetic resonance images, and a plurality of computed tomography images.

9. A computer program product comprising a non-transitory computer readable medium encoding instructions that, in response to execution by at least one processor, cause the processor to perform operations comprising:
   receiving a plurality of images of an abdominal region from an image capture device;
   identifying a bowel tissue from at least one of the plurality of images;
   identifying a peristaltic portion of the bowel tissue from the plurality of images;
   determining a peristalsis property of the bowel tissue based on the peristaltic portion, wherein the peristalsis property includes at least one of a percentage of the peristaltic portion within the bowel tissue and an amount of peristalsis in the peristaltic portion; and
   assessing a health of the bowel tissue based on the peristalsis property of the peristaltic portion.

10. The computer program product of claim 9, further causing the processor to calculate a health score of the bowel tissue based on the peristalsis property of the peristaltic portion.

11. The computer program product of claim 10, further causing the processor to determine a physical characteristic of the bowel tissue from the plurality of images and calculate the health score of the bowel tissue based on the physical characteristic.

12. The computer program product of claim 10, further causing the processor to determine a blood flow characteristic of the bowel tissue from the plurality of images and calculate the health score of the bowel tissue based on the blood flow characteristic.

* * * * *